United States Patent [19]

Prince et al.

[11] Patent Number: 5,290,540
[45] Date of Patent: Mar. 1, 1994

[54] METHOD FOR TREATING INFECTIOUS RESPIRATORY DISEASES

[75] Inventors: Gregory A. Prince, Potomac; Val G. Hemming, Gaithersburg, both of Md.

[73] Assignee: Henry M. Jackson Foundation for the Advancement of Military Medicine, Rockville, Md.

[21] Appl. No.: 877,095

[22] Filed: May 1, 1992

Related U.S. Application Data

[63] Continuation-in-part of Ser. No. 694,079, May 1, 1991, abandoned.

[51] Int. Cl.$^5$ .................................................. A61K 9/12
[52] U.S. Cl. ................................... 424/45; 424/85.8; 514/570; 514/885; 514/958; 514/959
[58] Field of Search .................... 424/47, 43, 45, 434, 424/85.8; 514/958, 570, 885, 959

[56] References Cited

U.S. PATENT DOCUMENTS

| 3,189,604 | 6/1965 | Beal, III et al. ................. 260/239.55 |
| 4,933,169 | 6/1990 | Shanbrom ............................ 424/43 |

FOREIGN PATENT DOCUMENTS

| 096153 | 10/1970 | Canada .................................. 424/45 |
| 0244402 | 3/1979 | Japan .................................. 424/434 |
| 919828 | 2/1963 | United Kingdom . |

OTHER PUBLICATIONS

G. Döring et al., "Immunologic Aspects of Cystic Fibrosis", Chest, 94:109S-115S (1988).
M. E. C. Horn et al., "Role of Viruses and Bacteria in Acute Wheezy Bronchitis in Childhood: A Study of Sputum", Archives of Disease in Childhood, 54:587-592, (1979).
G. Cuenant et al., "Efficacy of Endonasal Neomycin--Tixocortol Pivalate Irrigation in the Treatment of Chronic Allergic and Bacterial Sinusitis", 48:226-232 (1986).
S. A. Bozzette et al., "A Controlled Trial of Early Adjunctive Treatment With Corticosteroids for Pneumocystis Carinii Pneumonia in the Acquired Immun-modeficiency Syndrome", The New England Journal of Medicine, 323:1451-1457 (1990).
Abstract from Database WPI, Accession No. 80-004275 (17).
Alfonso R. Gennaro, "Pharmaceutical Sciences", 17th Edition, 1985, Easton, Pa. pp. 672, 960.
Raphael Dolin, "Antiviral Chemotherapy", Harrison's Principles of Internal Medicine, 12th Edition, vol. 1 pp. 493-495, 747-748.
Weatherall et al., "Infections", Oxford Textbook of Medicine, vol. 1, p.5.48.
Craig, et al., "Hormones and Drugs Affecting the Adrenal Cortex", Modern Pharmacology, 3rd Edition, p. 865.
Wyngaarden et al., "Parainfluenza Viral Diseases", Cecil Textbook Medicine, 18th edition, vol. 2, 1988, pp. 1760, 1766, 1790.
Hall et al., "Respiratory Syncytial Viral Infection in Children with Compromised Immune Function", The New England Journal of Medicine, vol. 315, No. 2, Jul. 10, 1986, pp. 77-81.
Takimoto et al., "Respiratory Syncytial Virus Infectious on an Adult Medical Ward", Arch Intern Med, vol. 151, Apr. 1991, pp. 706-708.
Taylor et al., "The Respiratory System", Family Medicine Principles and Practice, 3rd Edition, pp. 218-219.
Appleton & Lange, "Pneumonia", The Principles and Practice of Medicine, 22 Edition, p. 609.

(List continued on next page.)

Primary Examiner—Thurman K. Page
Assistant Examiner—Ray Bawa
Attorney, Agent, or Firm—Finnegan, Henderson, Farabow, Garrett & Dunner

[57] ABSTRACT

A method of treating pneumonia caused by a microorganism by administering directly into the lower respiratory tract of a host an amount of an anti-inflammatory agent effective to reduce inflammation is provided. The method may further include administering to a host an amount of an anti-infectious agent with activity against the microorganism effective to reduce the concentration of the microorganism.

22 Claims, No Drawings

OTHER PUBLICATIONS

Abraham I. Braude, "Pleuropulmonary Infections", Infectious Diseases and Medical Microbiology, 2nd Edition 1986, p. 822.

Hoeprich et al, "Viral Pneumonias", Infectious Diseases, 4th edition, pp. 357, 385–386.

Clark et al, "Drug Effects on the Respiratory Tract", Goth's Medical Pharmacology, 12th edition, pp. 513–514.

Bertram G. Katzung, Basic and Clinical Pharmacology, 3rd Edition, 1987, pp. 456–457.

Kalant et al, Principles of Medical Pharmacology, 5th edition, 1989, p. 481.

Eliot Marshall, "Visiting Experts Find the Mystery Disease of Naples is a Common Virus", Science, vol. 203, Mar. 9, 1979, pp. 980–981.

Leer et al, "Corticosteroid Treatment in Bronchiolitis", Amer J Dis Child, vol. 117, May 1969, pp. 495–503.

Thomas et al., "Infection of Gnotobiotic Calves with a Bovine and Human Isolate of Respiratory Syncytial Virus Modification of the Response by Dexamethasone", Archives of Virology 79, 67–77 (1984).

Nicolai et al., "Acute Viral Bronchiolitis in Infancy: Epidemiology and Management", Lung, (1990) Suppl pp. 396–405.

Amundson et al., "High-Dose Corticosteroid Therapy for Pneumocystis carinii Pneumonia in Patients with Acquired Immunodeficiency Syndrome", Southern Medical Journal, Jun., 1989, pp. 711–714.

Herman Chmel, "Pneumocystis cariini Pneumonia", Arch Intern Med. vol. 150, Sep. 1990, pp. 1793–1794.

Schiff et al., "Steroids for Pneumocystis carinii Pneumonia and Respiratory Failure in the Acquired Immunodeficiency Syndrome", Arch Intern Med. vol. 150, Sep. 1990, pp. 1819–1821.

James J. Rahal, "Corticosteroids as Adjunctive Therapy for Pneumocystis Pneumonia in Patients with AIDS", The New England Journal of Medicine, Jun. 6, 1991, p. 1666.

Charles Reed, "Aerosol; Steroids as Primary Treatment of Mild Asthma", The New England Journal of Medicine, vol. 325, No. 6, pp. 425–426.

Haahtela et al, "Comparison of a B2-Agonist, terbutaline, with an Inhaled Corticosteroid, Budesonide, in Newly Detected Asthma", The New England Journal of Medicine, Aug. 8, 1991, pp. 388–392.

Maayan et al., "The Functional Response of Infants with Persistant Wheezing to Nebulized Beclomethasone Dipropionate", Pediatric Pulmonology, vol. 2, No. 1—Jan.14 Feb., 1986, pp. 9–14.

McGowan et al., "Guidelines for the Use of Systemic Glucocorticosteroids in the Management of Selected Infections", J. of Infectious Diseases, vol. 165, pp. 1–13 (1992).

FDA Bulletin, Dec. 1991, pp. 2–3.

Gennaro, (1985), Remington's Pharmaceutical Sciences, Mack & Co., p. 1676.

METHOD FOR TREATING INFECTIOUS RESPIRATORY DISEASES

This application is a continuation-in-part of U.S. Ser. No. 07/694,079, filed May 1, 1991, now abandoned, the contents of which are hereby incorporated by reference.

BACKGROUND OF THE INVENTION

The present invention is related generally to the therapy of lower respiratory tract diseases caused by respiratory viruses or other infectious agents. More particularly, the present invention is related to a novel, effective, and rapid method of treating lower respiratory tract disease caused particularly by parainfluenza virus type 3 (PIV3) or adenovirus type 5 (Ad-5) by direct administration of corticosteroids or anti-inflammatory drugs into the lower respiratory tract. One embodiment of the invention is primarily directed to a method of treating lower respiratory tract infections that alters the immune response to infection, and is not concerned with the presence of viable infectious agents per se. However, the method of the present invention can also be used in combination with anti-infective therapy.

Another embodiment of the invention includes anti-infective therapy. This embodiment is directed to a method of treating lower respiratory tract disease caused particularly by respiratory syncytial virus (RSV) and parainfluenza virus type 3 (PIV3) by administering a combination of an anti-infectious agent and an anti-inflammatory agent. Therapy using a topically applied combination of an anti-infectious agent plus an anti-inflammatory agent dramatically reduces both components of pulmonary pathology, namely alveolar inflammation (interstitial pneumonia) and bronchiolar inflammation (bronchiolitis), and accelerates clearance of the infectious agent.

Lower respiratory tract disease caused by viruses and other infectious agents is a serious problem in all ages, particularly in the very young and the elderly. Respiratory syncytial virus (RSV) and parainfluenza virus type 3 (PIV3) are the leading causes of pulmonary disease in infants and children worldwide (Chanock, 1990, in Fields et al., eds., *Virology*, 2d ed., New York, Raven Press, pp. 963-988; McIntosh, 1990, in Fields et al., eds., *Virology*. 2d ed., New York, Raven Press, pp. 1045-1072). While the clinical and financial burdens of the two viruses are uncertain, a 1985 study by the National Academy of Sciences estimated that nearly 10,000 deaths and medical costs in excess of one billion dollars are due to RSV and PIV3 each year in the United States (*New Vaccine Development. Establishing Priorities. Vol. 1. Diseases of Importance in the United States*, Washington, D.C., National Academy Press, 1985, pp. 385-409). Clinical and financial burdens in other countries are assumed to be at least as great as in this country, although no estimates have been published. In spite of their importance, however, no vaccine has been developed against either virus.

Currently there is no licensed therapy for PIV3 or Ad-5 lower respiratory disease and the licensed therapy for treating diseases caused by other respiratory viruses is of limited efficacy. In the case of respiratory syncytial virus (RSV), treatment requires the delivery of ribavirin (1-beta-D-ribofuranosyl-1,2,4,-triazole-3-carboxamide) by small particle aerosol for 12-20 hours a day for at least 3 days (Hall et al., 1983 *New Eng. J. Med.* 308:1443-1447; Taber et al., 1983 *Pediatrics* 72:613-618). This treatment involves intervention in the replicative cycle of the RSV. Ribavirin appears to be of only marginal efficacy, and its use has recently come under increasing criticism (Khan, 1991 *Am. Rev. Resp. Dis.* 143:A510).

Inhaled corticosteroids (e.g., beclamethasone) are commonly used in the treatment of allergic asthma (reactive airway disease). However, corticosteroid therapy was not found to be beneficial in the treatment of viral bronchiolitis, especially that caused by RSV (Leer et al., 1969 *Amer. J. Dis. Child.* 117:495). Indeed, the prevailing wisdom is that the use of corticosteroids (and presumably other anti-inflammatory agents) during respiratory viral infections is contraindicated (Stecenko, 1987, *Contemp. Pediat.* 4:121; Thomas et al., 1984, *Arch Virol.* 79:67-77; Sieber, 1977, *Pediat. Res.* 11:230; Mandell, Douglas & Bennett, *Principles and Practice of Infectious Diseases*, Third Edition, 1990, p. 1274). It should be noted, however, that all of these reports were based upon the use of systemically administered corticosteroids. The use of topically administered corticosteroids, or other anti-inflammatory agents such as ibuprofen or indomethacin, in the treatment of infectious respiratory tract disease has not been addressed in the scientific literature.

Recent reports show that the major component of pulmonary disease caused by PIV3 and Ad-5 is the host immunologic response to infection, rather than direct viral injury to host tissues (Porter et al., 1991 *J. Virol.* 65:103-111; Ginsberg et al., 1991 *Proc. Nat. Acad. Sci. USA* 88:1651-1655). Therefore, elimination of virus from infected tissues, such as in case of ribavirin therapy, may not be expected to reverse host responses already triggered by infection. The host immunologic response is also triggered by many bacterial, fungal and parasitic pulmonary infections, as exemplified by *Mycoplasma pneumoniae* or *Pneumocystis carinii* pneumonias.

The use of anti-inflammatory agents, particularly corticosteroids, in infectious diseases has long been controversial (McGowan, 1992, *J. Infect. Dis.* 165:1-3), presumably due to the fact that suppression of the inflammatory response can lead to impairment of the host's ability to clear the infectious agent. However, three sets of observations have recently called into question the conventional wisdom. First, high doses of systemically administered corticosteroids may have a lifesaving effect in viral meningitis (McGowan, 1992 *J. Infect. Dis.* 165:1-3). Second, it has become evident that the use of high doses of corticosteroids, in conjunction with chemotherapeutic agents, has lifesaving potential in many cases of *Pneumocystis carinii* pneumonia in HIV patients (Rahal, 1991 *New Eng. J. Med.* 324:1666). Finally, it has become apparent that at least three major respiratory viruses (RSV, PIV3, and type 5 adenovirus), which cause minimal direct viral lysis of host tissues, produce a pulmonary disease which is predominantly host-mediated. That is, most, if not all, of the pulmonary pathology is due to the accumulation of host inflammatory and immune cells in lung tissues, rather than the direct destruction of host tissue by the viruses (Ginsberg, 1989 *Proc. Nat. Acad. Sci. USA* 86:3823-3827; Ginsberg, 1990 *Proc. Nat. Acad. Sci. USA* 87:6191-6195; Porter, 1991 *Am. J. Pathol.* 93:185-205; Prince, 1978 *J. Virol.* 65:103-111).

Of direct relevance to the current proposal are observations from the mouse model of type-5 adenovirus pneumonia that cytokine levels (tumor necrosis factor, interleukin-1, and interleukin-6) correlate with pulmonary pathology (Ginsberg, 1991 *Proc. Nat. Acad. Sci. USA* 88:1651-1655). Suppression of these cytokines with specific antiserum causes partial ablation of the pathologic process. Corticosteroid treatment of mice prior to viral challenge results in suppression of all three of these cytokines and nearly complete prevention of pneumonia.

The theoretical basis of the proposed combination of anti-infective and anti-inflammatory therapy is the assumption that antiviral therapy, alone, would be unlikely to have a dramatic effect on a pulmonary disease process caused primarily by the host inflammatory response. Indeed, the demonstration in experimental models, both of RSV and PIV3, that pulmonary pathology reaches its maximum two days after peak viral titers (Porter, 1991 *J. Virol.* 65:103-111,; Prince, 1978 *Am. J. Pathol.* 93:185-205,) suggests that viral titers may already be declining when patients are hospitalized with RSV or PIV3 pneumonia. Since there is no drug currently identified with both antiviral (RSV and PIV3) and anti-inflammatory properties, a combination of a potent antiviral (human immunoglobulin, IgG) and a potent anti-inflammatory (corticosteroid) was used.

Two viruses were chosen for the anti-infective therapy, parainfluenza virus type 3 (PIV3) and respiratory syncytial virus (RSV). These viruses were chosen for the following reasons: (1) RSV is the most important cause of infectious pneumonia in infants, and PIV3 is the next most important cause; and (2) antiviral therapies have been demonstrated against both viruses. In the case of RSV, ribavirin has been licensed for topical therapy and is in widespread clinical use; additionally, purified antibody with high levels of anti-RSV activity has been shown effective in eliminating pulmonary RSV when used topically (Prince et al., 1987 *J. Virol.* 61:1851-1854; Prince et al., U.S. Pat. No. 4,800,078).

The examples and discussion provided in this application demonstrate that (1) combined topical therapy using an anti-infective agent and a corticosteroid dramatically reduces pulmonary pathology caused by each of the two viruses, RSV and PIV3; and (2) corticosteroids are effective when used either with an antiviral chemotherapeutic agent such as ribavirin or an antiviral biologic agent such as purified antibody.

The invention provides an effective method of treating lower respiratory tract disease which targets the injurious immunologic host response. As discussed above, the use of anti-inflammatory agents to treat infections is usually not recommended because the inflammatory response is part of the immune system, and one would not expect suppressing part of the immune system to be of benefit in treating an infection. This invention unexpectedly provides a method of treating lower respiratory tract disease which uses anti-inflammatory agents to reduce the host's immune response to the disease.

Applicants' studies have shown that a therapeutic approach combining topically administered antiviral and anti-inflammatory agents accelerates the clearance of virus from infected laboratory animals, while reversing the disease process in their lungs. These studies have employed human immunoglobulin (IgG) as the antiviral agent, and triamcinolone acetonide as the anti-inflammatory agent; however, other antiviral and anti-inflammatory agents may also be used. IgG and corticosteroids are already in common clinical use for other indications and are relatively inexpensive. Clinical trials have not been performed. However, based on the dramatic results of the combined anti-infective and anti-inflammatory therapy, the invention should provide a dramatic, yet inexpensive, treatment of the most common forms of infant and childhood pulmonary disease.

SUMMARY OF THE INVENTION

It is, therefore, an object of the present invention to provide a therapeutic device, comprising means for delivering directly into the lower respiratory tract of a subject afflicted with disease caused by PIV3, Ad-5, or other infectious agents, an effective amount of a corticosteroid or an anti-inflammatory drug in the form of small particle aerosol, so that said disease or symptoms thereof are either alleviated, controlled, or cured.

It is a further object of the present invention to provide a more effective, simple and quick-acting method of treating infectious respiratory disease caused by viral, bacterial, fungal, and parasitic agents such as those described above, than heretofore available therapeutic modalities.

Another object of the invention is to provide a method of treating lower respiratory tract disease in a host, susceptible to or suffering from a lower respiratory tract disease caused by an infectious agent. This method comprises administering to the host an amount of an anti-infectious agent with activity against the infectious agent and topically administering to the host an amount of an anti-inflammatory agent effective to produce a therapeutic effect against the disease.

Other objects and advantages of the invention will become evident from the following detailed description of the invention.

DETAILED DESCRIPTION OF THE INVENTION

The above and various other objects and advantages of the present invention are achieved by (1) a therapeutic device, comprising means for delivering directly into the lower respiratory tract of a subject afflicted with disease caused by PIV3, Ad-5, or other infectious agents, an effective amount of a corticosteroid or other anti-inflammatory drug such as ibuprofen or indomethacin, in the form of small particle aerosol, so that said disease or symptoms thereof are either alleviated, controlled, or cured; and (2) a method of treating respiratory disease, comprising topically administering to a host suffering from pulmonary disease caused by infectious agents such as parainfluenza virus type 3 (PIV3) or adenovirus type 5 (Ad-5), an effective amount of a corticosteroid or a non-steroidal anti-inflammatory drug to produce therapeutic effect against pulmonary disease.

One embodiment of the invention provides a method of treating lower respiratory tract disease in a host, susceptible to or suffering from a lower respiratory tract disease caused by an infectious agent. This method comprises administering to the host an amount of an anti-infectious agent with activity against said infectious agent and topically administering to the host an amount of an anti-inflammatory agent effective to produce a therapeutic effect against said disease. This method is preferred because it includes both an anti-inflammatory agent and an anti-infectious agent. The anti-inflammatory agent reduces the host's inflammatory reaction to the infection and the anti-infectious agent fights the infection.

Another embodiment of the invention provides a method of treating lower respiratory tract disease in a host, susceptible to or suffering from a lower respiratory tract disease caused by an infectious agent, comprising topically administering to the host an amount of an anti-inflammatory agent effective to produce a therapeutic effect against said disease. Preferably, the anti-inflammatory agent is administered directly into the lower respiratory tract of the host.

The anti-infectious agent may be administered topically, orally, intravenously, or intraperitoneally. Topical administration is preferred. The primary advantage of topical administration of a therapeutic drug is that higher concentrations of drug may be delivered to affected tissues with a lower total dose to the patient than is necessary with systemic administration, thus potentially circumventing many of the known side effects of systemic administration of high doses of drugs such as corticosteroids.

In a preferred embodiment, the anti-inflammatory agent and the anti-infectious agent are administered directly into the lower respiratory tract of the host. The anti-inflammatory agent and/or the anti-infectious agent may be administered intranasally. The anti-inflammatory agent and/or the anti-infectious agent may be administered intranasally in the form of aerosol particles.

The anti-inflammatory agent may be administered at a dosage of from 0.1 $\mu$g to 1000 mg/kg body weight of the host. A preferred range for the anti-inflammatory agent is a dosage of from 2 $\mu$g to 0.2 mg/kg body weight of the host.

The anti-infectious agent may be administered at a dosage of from 0.1 $\mu$g to 1000 mg/kg body weight of the host. A preferred range for the anti-infectious agent is a dosage of from 2 $\mu$g to 20 mg/kg body weight of the host.

The anti-inflammatory agent may be a corticosteroid. Suitable corticosteroids are cortisone, hydrocortisone, triamcinolone, dexamethasone, or beclamethasone. Triamcinolone is a preferred corticosteroid.

The corticosteroid may be administered at a dosage of from 0.01 to 1000 mg/kg body weight of the host. A preferred range for the corticosteroid is a dosage of from 0 5 to 50 mg/kg body weight of the host.

The anti-inflammatory agent may be indomethacin, ibuprofen, or acetylsalicylic acid. The anti-inflammatory agent may be an anti-cytokine agent. In turn, the anti-cytokine agent may be a monoclonal or polyclonal antibody directed against a cytokine. The cytokines may be tumor necrosis factor, an interleukin, or an interferon.

The infectious agent may be a virus. Viruses to which the invention is applicable include influenza virus type A, influenza virus type B, influenza virus type C, parainfluenza virus type 1, parainfluenza virus type 2, parainfluenza virus type 3, respiratory syncytial virus, a respiratory coronavirus, or a respiratory adenovirus. Applicants have conducted experiments that demonstrate the suitability of the invention in treatment of disease caused by parainfluenza virus type 3, respiratory syncytial virus, or adenovirus type 5.

The infectious agent may be a bacterium. Bacteria to which the invention is applicable include *Streptococcus pneumoniae, Haemophilus influenzae, Staphylococcus aureus,* klebsiella, or legionella.

The infectious agent may be a fungus. Fungi to which the invention is applicable include *Coccidioides immitus, Histoplasma capsulatum,* or *Cryptococcus neoformans.* The infectious agent may be *Pneumocystis carinii.* The infectious agent may be a rickettsia, such as Q fever or typhus.

The anti-infectious agent may be an antibody to the infectious agent. The antibody may be a polyclonal antibody or monoclonal antibody. The monoclonal antibody may be derived from mouse cells, human cells, or genetically-engineered cells.

The anti-infectious agent may be human immunoglobulin which comprises antibodies to said infectious agent. The antibodies in the human immunoglobulin may be monoclonal, polyclonal, or genetically-engineered antibodies. In a preferred embodiment, the human immunoglobulin is human immunoglobulin G. In another preferred embodiment, the anti-infectious agent is human immunoglobulin G which comprises polyclonal antibodies. The human immunoglobulin G may be administered at a dosage of from 0.1 $\mu$g to 100 mg/kg body weight of the host. A preferred dosage for the human immunoglobulin G is from 0.1 mg to 20 mg/kg body weight of the host.

The human immunoglobulin may be human immunoglobulin A or human immunoglobulin M. In a preferred embodiment, the human immunoglobulin A or M comprise monoclonal antibodies.

In another preferred embodiment, the anti-infectious agent is human immunoglobulin which comprises antibodies to a virus, especially respiratory syncytial virus or parainfluenza virus type 3.

The anti-infectious agent may be an anti-bacterial agent such as a macrolide, a penicillin, a cephalosporin, or a tetracycline. The anti-infectious agent may be an antifungal agent such as amphotericin b, fluconazole, or ketoconazole. The anti-infectious agent may be an antiparasitic agent such as trimethoprim, pentamidine, or a sulfonamide. The anti-infectious agent may be an antiviral agent such as ribavirin or amantidine.

The host may be a mammal, especially a human.

A preferred embodiment of the invention provides a method of treating lower respiratory tract disease in a host, susceptible to or suffering from a lower respiratory tract disease caused by a virus, comprising administering to the host an amount of an anti-viral agent with activity against said virus and administering directly to the lower respiratory tract of the host an amount of an anti-inflammatory agent effective to produce a therapeutic effect against said disease. The anti-viral agent may be administered directly to the lower respiratory tract of the host. The virus may be respiratory syncytial virus or parainfluenza virus type 3. The anti-viral agent may be ribavirin or human immunoglobulin G which comprises antibodies to said virus.

In another preferred embodiment, the invention provides a method of treating lower respiratory tract disease in a human, susceptible to or suffering from a lower respiratory tract disease caused by respiratory syncytial virus or parainfluenza virus type 3, comprising administering directly into the lower respiratory tract of the human an amount of an anti-inflammatory agent and an amount of human immunoglobulin G effective to produce a therapeutic effect against said disease. The anti-inflammatory agent and the human immunoglobulin G may be administered in the form of aerosol particles. The anti-inflammatory agent may be a corticosteroid. In turn, the corticosteroid may be triamcinolone.

In another preferred embodiment, the invention provides a method of treating lower respiratory tract disease in a host, susceptible to or suffering from a lower respiratory tract disease caused by parainfluenza virus type 3, adenovirus type 5, or respiratory syncytial virus, comprising administering directly into the lower respiratory tract of the host an amount of an anti-inflammatory agent effective to produce a therapeutic effect against said disease.

One embodiment of the invention provides a medication that comprises aerosol particles comprising an anti-infectious agent and an anti-inflammatory agent. This medication is useful in treating lower respiratory tract disease.

Another embodiment of the invention provides a device that expels aerosol particles. The aerosol particles comprise an anti-infectious agent and an anti-inflammatory agent.

One embodiment of the invention provides a device comprising a therapeutic means that delivers directly into the lower respiratory tract of a host susceptible to or suffering from a lower respiratory tract disease caused by an infectious agent, an amount of an anti-infectious agent and an anti-inflammatory agent effective to produce a therapeutic effect against said disease. This device may have a means comprising a small particle aerosol.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned are incorporated herein by reference. Unless mentioned otherwise, the techniques employed or contemplated herein are standard methodologies well known to one of ordinary skill in the art. The materials, methods, and examples are illustrative only and not limiting.

The term "small particle aerosol" as used herein means particles of pharmaceutically acceptable vehicle less than 10 microns in size, preferably less than 5 microns in size, and more preferably less than 2 microns in size containing the drug(s) to be delivered to the lower respiratory tract.

EXAMPLES

Animals

Inbred cotton rats (*Sigmodon hispidus*) were obtained from the colony of Virion Systems, Inc. Adult animals, free from specific rodent pathogens, were used. Animals were housed in large polycarbonate rat cages with a bedding of hardwood chips, and fed a diet of standard rat chow and water. Adult animals ranging from 1 to 8 months of age were used. No age-related differences in response to infection or treatment were seen.

Drug Testing

Hydrocortisone acetate was selected as the prototypical corticosteroid for the anti-inflammatory studies. Cotton rats were infected (Day 0) by intranasal instillation of PIV3 ($10^6$ pfu/animal) or Ad-5 ($10^9$ pfu/animal). Animals were anesthetized with methoxyflurane, and the inoculating virus was delivered in a volume of 0.1 ml/100 gm body weight of the animal. On Day 3, animals were anesthetized with methoxyflurane, and hydrocortisone acetate (50 mg/ml) was instilled intranasally in a volume of 0.1 ml/100 gm body weight. The same treatment with hydrocortisone acetate was repeated once per day on Days 4 and 5. For purposes of comparison, control animals were infected concurrently on Day 0, but received no treatment on Days 3, 4, or 5. On Day 6, all animals were euthanized by carbon dioxide intoxication.

In order to demonstrate the general applicability of the method of the present invention, other corticosteroids were also tested. These included dexamethasone acetate (8 mg/ml) and triamcinolone acetonide (40 mg/ml). Of course, other corticosteroids or anti-inflammatory agents known to one of ordinary skill in the art could also be used.

Histology

Lungs were removed from the thorax and inflated through the trachea with neutral buffered formalin. Histologic sections were made by following standard procedures and stained with hematoxylin and eosin (H&E).

Therapeutic efficacy of topically administered drugs

Two sets of experiments were performed using hydrocortisone acetate. In the first, animals were infected with PIV3 and subsequently treated with topically administered hydrocortisone acetate. In the second, animals were infected with Ad-5 and subsequently treated with topically administered hydrocortisone acetate.

Topical administration was accomplished by anesthetizing the animals, holding them in a vertical posture, and instilling a solution containing corticosteroid onto the nares. A total volume of 0.1 ml/100 gm body weight was used. Previous studies showed that this method of instillation resulted in the rapid deposition of inoculum into the lungs (Prince et al., 1978, *Am. J. Pathol.* 93:771–792). A small-particle ultrasonic nebulizer (Portasonic 8500D, DeVilbiss Co., Somerset, PA) was used to demonstrate the feasibility of generating an aerosol of hydrocortisone acetate solution. However, for human administration it is desirable to use a small particle aerosol delivered by a device that could be triggered by inhalation or used synchronously with the inhalation phase of ventilation for patients on a ventilator. Such a device could deliver aerosol from powder (spinhaler) or liquid. Since many patients, especially young infants and debilitated adults, may have diminished respiratory inhalation vigor, it is important to synchronize aerosol generation with inhalation. This could be accomplished by having inhalation trigger the aerosol delivery to the airway (nasal prongs, oral tube, etc.). The trigger mechanism could include negative pressure from inhalation, chest movement, or electrical triggering synchronized with diaphragmatic contraction. Electrical leads used to monitor respirations could be used to synchronize aerosol generation to be triggered at the first initiation of diaphragmatic contraction and respiration. Any form of aerosol generator is suitable if aerosol delivery is synchronized with inhalation and appropriate particle size is consistently generated.

Therapeutic efficacy is determined by comparing two parameters in treated versus control animals: (1) the percentage of alveoli on a single H&E-stained coronal section of lungs containing interstitial and/or intraalveolar pathology; and (2) the percentage of bronchioles, on the same section of lungs, affected by peribronchiolar lymphocytic infiltration.

The therapeutic effect on PIV3 pulmonary disease is demonstrated by the results presented in Table 1. "Treated" denotes treatment with hydrocortisone acetate as described above. The raw data from which the results in the following tables were extracted are presented in Appendix A.

TABLE 1

| Experiment | Group | # Animals | % Alveoli | % Bronchioles |
|---|---|---|---|---|
| 1 | Control | 4 | 25 | 61 |
|   | Treated | 4 | 11 | 9 |
| 2 | Control | 4 | 41 | 65 |
|   | Treated | 4 | 30 | 15 |
| 6 | Control | 3 | 75 | 61 |
|   | Treated | 3 | 20 | 24 |
| 7 | Control | 6 | 82 | 95 |
|   | Treated | 3 | 37 | 14 |

The therapeutic effect on Ad-5 pulmonary disease is summarized in Table 2.

TABLE 2

| Experiment | Group | # Animals | % Alveoli | % Bronchioles |
|---|---|---|---|---|
| 3 | Control | 4 | 43 | 71 |
|   | Treated | 4 | 9 | 16 |
| 4 | Control | 4 | 70 | 91 |
|   | Treated | 4 | 38 | 39 |

As shown by the data, in each instance, both with PIV3 and Ad-5, there was a significant reduction in alveolar and bronchiolar inflammation following treatment by topically administered hydrocortisone acetate. The net reduction in disease caused by PIV3 ranged from 27-56% for alveolar inflammation, and 77-85% for bronchiolar inflammation. The net reduction in disease caused by Ad-5 ranged from 46-79% for alveolar inflammation, and 57-77% for bronchiolar inflammation. There was no evidence of exacerbated disease in any hydrocortisone acetate-treated animals.

Results obtained with PIV3 infection, using topically administered dexamethasone acetate or triamcinolone acetonide are presented in Table 3:

TABLE 3

| Experiment | Group | # Animals | % Alveoli | % Bronchioles |
|---|---|---|---|---|
| 5 | Control | 4 | 70 | 83 |
|   | Dexamethasone | 3 | 50 | 21 |
|   | Triamcinolone | 4 | 24 | 9 |

Compared to control values, dexamethasone acetate reduced alveolar inflammation by 28% and bronchiolar inflammation by 75%, and triamcinolone acetonide reduced alveolar inflammation by 80% and bronchiolar inflammation by 89%.

The effect of other infectious agents and drugs are evaluated in the same manner as described above. Anti-inflammatory drugs include such non-steroidal anti-inflammatory agents as indomethacin, ibuprofen and the like.

Further experiments were performed to investigate the use of an anti-infectious agent in combination with an anti-inflammatory agent. The following procedure was used.

Animals

Inbred cotton rats (*Sigmodon hispidus*), as described above, were used.

Drug Testing

Triamcinolone acetonide was selected as the prototypical corticosteroid for the combined anti-infective and anti-inflammatory studies. As shown above, a variety of corticosteroids demonstrate similar anti-inflammatory action in infectious pulmonary disease. Therefore, the use of triamcinolone acetonide is merely by example of a general property of corticosteroids. Cotton rats were infected (Day 0) by intranasal instillation of PIV3 ($10^6$ pfu/animal) or RSV ($10^5$ pfu/animal). Animals were anesthetized with methoxyflurane, and the inoculating virus was delivered in a volume of 0.1 ml/100 gm body weight of the animal. On Day 3, animals were anesthetized with methoxyflurane, and treated by intranasal instillation of anti-infective agent or a combination of anti-infective agent and corticosteroid, in a volume of 0.1 ml/100 gm body weight. The same treatment was repeated once per day on Days 4 and 5. For purposes of comparison, control animals were infected concurrently on Day 0, but received no treatment on Days 3, 4, or 5. On Day 6, the time of maximum pulmonary pathology in infected, untreated animals, all animals were euthanized by carbon dioxide intoxication.

Histology

The same histologic procedure as described above was used.

Therapeutic efficacy of combined therapy

Three experiments were performed using combined therapy: (1) anti-PIV3 antibody (100 mg/kg) and triamcinolone acetonide (4 mg/kg) were used to treat PIV3 infection; (2) anti-RSV antibody (25 mg/kg) and triamcinolone acetonide (4 mg/kg) were used to treat RSV infection; (3) ribavirin (20 mg/kg) and triamcinolone acetonide (4 mg/kg) were used to treat RSV infection. All agents were administered topically as described above in "Drug Testing". Therapeutic efficacy was determined by comparing the following parameters in the treated and control animals: (1) in the case of PIV3, the percentage of alveoli on a single H&E-stained coronal section of lungs containing interstitial and/or intraalveolar pathology (RSV does not cause significant alveolar disease in the cotton rat); and (2) in the case of PIV3 and RSV, the percentage of bronchioles affected by peribronchiolar lymphocytic infiltration.

As shown in Table 4, animals treated with triamcinolone showed dramatically decreased pulmonary pathology. The Student t-test, the standard test for paired data, has been applied to these data to determine the level of significance of reduction of disease. In all reported studies, each group contained a minimum of four animals.

TABLE 4

| | Pulmonary Pathology, PIV3 | |
|---|---|---|
| Treatment | % Alveoli | % Bronchioles |
| Untreated | 70 | 83 |
| Triamcinolone | 24 ($p < 0.01$) | 9 ($p < 0.001$) |

However, viral titrations showed that triamcinolone treatment, while reversing pulmonary pathology, both increased and prolonged viral shedding (Table 5).

TABLE 5

| | Pulmonary Viral Titers (pfu/gm), PIV3 | | |
|---|---|---|---|
| Treatment | Day 6 | Day 8 | Day 10 |
| Untreated | $10^{2.6}$ | $<10^2$ | $<10^2$ |
| Triamcinolone | $10^{5.3}$ | $10^{4.9}$ | $10^{4.3}$ |

Similar results were seen when cotton rats infected with RSV were treated with triamcinolone. That is, pulmonary pathology was dramatically reduced, while viral shedding was increased and prolonged.

In another series of experiments, cotton rats infected either with PIV3 or RSV were treated (on days 3, 4, and 5) with topically administered triamcinolone, with IgG containing high antiviral activity, or with a combination of triamcinolone and IgG (Tables 6 and 7). RSV causes moderate bronchiolitis in *S. Hispidus* but no significant interstitial pneumonia.

TABLE 6

| | Pulmonary Pathology and Viral Titers, PIV3 | | |
|---|---|---|---|
| Treatment | % Alveoli | % Bronchioles | Day 6 Titer |
| Untreated | 31 | 74 | $10^{3.1}$ |
| Triamcinolone | 10 ($p < 0.05$) | 6 ($p < 0.001$) | $10^{4.6}$ |
| IgG | 75 (N.S.*) | 92 (N.S.) | $<10^2$ |
| Triam. + IgG | 7 ($p < 0.05$) | 2 ($p < 0.025$) | $10^{2.4}$ |

*N.S denotes not significant.

TABLE 7

| | Pulmonary Pathology and Viral Titers, RSV | |
|---|---|---|
| Treatment | % Bronchioles | Day 6 Titer |
| Untreated | 22 | $10^{3.4}$ |
| Triamcinolone | 0.5 ($p < 0.025$) | $10^{4.8}$ |
| IgG | 27 (N.S.) | $<10^2$ |
| Triam. + IgG | 0.5 ($p < 0.025$) | $<10^2$ |

The results of these studies led to the following conclusions:

1. Treatment with triamcinolone reduced pulmonary pathology, but prolonged and increased viral shedding.
2. Treatment with IgG reduced viral titers to undetectable or near-undetectable levels, but had no effect on pulmonary pathology.
3. Combined treatment, utilizing triamcinolone and IgG together, resulted in a dramatic decrease in pulmonary pathology and accelerated viral clearance, thus combining the advantages of each individual treatment modality.

A final experiment tested combined therapy of RSV disease using ribavirin as the antiviral agent (Table 8).

TABLE 8

| | Pulmonary Pathology and Viral Titers, RSV | |
|---|---|---|
| Treatment | % Bronchioles | Day 6 Titer |
| Untreated | 38 | $10^{3.8}$ |
| Triamcinolone | 0 ($p < 0.001$) | $10^{5.2}$ |
| Ribavirin | 48 (N.S.) | $10^{4.2}$ |
| Triam. + Ribavirin | 0.5 ($p < 0.01$) | $10^{5.1}$ |

Ribavirin, although licensed as a therapeutic agent for RSV infection, is minimally effective under these conditions in the cotton rat, an observation which agrees with recently published data from another laboratory using the cotton rat model (Gilbert et al., 1992 *Antiviral Research* 17:33–42).

As was the case with IgG, ribavirin alone had no effect on pulmonary pathology. Unlike IgG, however, ribavirin did not reduce viral titers. Furthermore, combined therapy using ribavirin and triamcinolone, while reducing pulmonary pathology, resulted in increased viral titers, indicating that IgG is clearly superior to ribavirin as an antiviral agent, and that combined ribavirin/corticosteroid therapy is not as effective as combined IgG/corticosteroid therapy. The most preferred method of treating diseases of the lower respiratory tract is with a combination of IgG and triamcinolone.

Traditional treatment of the two most important causes of viral pulmonary disease of infants, RSV and PIV3, consists of administering an antiviral agent to the respiratory tissues. However, the effect of antiviral agents has heretofore been described only in terms of reduction in viral titer, and not in terms of reversing pulmonary histopathology. Using purified antibody against RSV or PIV3, applicants have shown that viral titers may be reduced within 24 hours, but that antibody does not reverse pulmonary pathology in the case of either virus. Ribavirin, although licensed for therapeutic use against RSV, has not shown a dramatic antiviral effect in experimental animals, either in our laboratory or by other investigators. Nevertheless, it was tested because it is the only drug licensed for therapeutic use against RSV. It neither effected a significant reduction in pulmonary RSV titers, nor affected pulmonary pathology.

By contrast, the concurrent use of an antiviral agent (either antibody or ribavirin) and a corticosteroid (triamcinolone acetonide), applied topically to the pulmonary tissues, resulted in dramatic decreases in viral titer (in the case of antibody), and virtual elimination of pulmonary pathology (in the cases both of ribavirin and antibody). Therefore, the novel use of combined therapy carries the advantages of accelerated virus clearance, and reversal of pulmonary disease.

The results presented herein clearly establish the therapeutic efficacy of the methods, medications, and devices of the present invention against pulmonary disease.

Of course, the present invention opens a new vista for more effective treatment of viral lower respiratory tract disease through the topical administration of corticosteroids and anti-inflammatory drugs and the combination of anti-infective and anti-inflammatory therapy. It must be noted that a definitive advantage of the new treatment modality disclosed herein is that a therapeutic agent which is already licensed for parenteral use in humans can now also be administered by inhalation for a new therapeutic indication.

It is understood that the examples and embodiments described herein are for illustrative purposes only and that various modifications or changes in light thereof will be suggested to persons skilled in the art and are to be included within the spirit and purview of this application and scope of the appended claims.

MATERIALS AND METHODS

Stocks of respiratory viruses (such as RSV and PIV3) were prepared by growing appropriate monolayers of susceptible cells in tissue culture and then inoculating the cells with seed virus. For example, HEp2 cells were inoculated into flat-bottomed flasks suspended in tissue culture media to facilitate cell replication. The cells were incubated until a confluent monolayer of cells covered the bottom of the flask. At the point in time when confluence was achieved (about 3 or 4 days) the cells were inoculated with the seed stock of the virus. The infected bottle was then incubated, in a temperature-controlled incubator in a 5% carbon dioxide atmosphere, for 3 to 4 days when the RSV-infected cells begin to express generalized infection. At that point the bottle and its contents were frozen to minus 80° C. Freezing lyses the virally infected cells and frees virus. The contents of the bottle were centrifuged to separate the cellular debris from the supernatant which contained substantial amounts of infectious virus (often from 4.5 to 5.5 $\log_{10}$ plaque-forming units (pfu) of virus/milliliter). This material was frozen at a minus 80° C. until used in the various assays or animal experiments.

Cotton rats were challenged to induce infection in the following manner. The frozen virus (usually at a concentration of $10^5$ pfu/ml) was thawed and then immediately instilled (0.05 ml/nostril) into anesthetized cotton rats. RSV or PIV3 infections did not make the animals perceptibly ill. However, when euthanized on the fourth or fifth day of infection, about $10^5$ pfu of virus/gram of lung tissue was recovered. Lungs were removed from the animal, homogenized in tissue culture fluid, and cultured on HEp2 monolayers. The amount of virus was then quantified.

Neutralizing antibody titers (titers for RSV or PIV3) in human or animal serum or pooled immunoglobin (IgG) were determined in the following manner. Known quantities of the virus were mixed with various dilutions of serum or IgG and incubated for an hour. The mixture was then poured onto a HEp2 cell monolayer and allowed to fix for an hour; the monolayer was washed with culture media and an overlay was added to immobilize the virus. The cells were cultured for about 5 days and then the amount of virus neutralized was enumerated by counting the number of plaques. Each plaque is considered to be one virus particle that was not inactivated by antibodies in the serum or IgG preparation. The results of these assays were expressed as geometric mean titers. In the literature this is called a 60% plaque reduction neutralization titer.

Cotton rats (Sigmodon hispidus) are currently produced by Virion Systems, Inc., Bethesda, Md., for commercial sale. Virion Systems, Inc. is licensed by the United States Department of Agriculture for this function. Breeding stock of the same species is also available from the National Center for Research Resources, Bethesda, Md., which is part of the National Institutes of Health.

A single pool of purified human IgG, with known neutralizing antibody titer, was used with each virus throughout the experiments, to minimize experimental variability. Preliminary experiments were conducted to determine the dose of each IgG preparation which, when given three days post-infection, reduced pulmonary viral titers to undetectable levels within 24 hours. Once determined, this dose was used in all subsequent experiments.

Viruses. Two prototype viruses, the Long strain of RSV (originally isolated in 1956) and strain 23451 of PIV3 (isolated in 1964) were used in all studies. A pool was prepared of each strain. The RSV pool contained $10^{5.5}$ pfu/ml, while the PIV3 pool contained $10^{6.5}$ pfu/ml. Both pools were found to be free of bacteria, mycoplasmas, and extraneous viruses by culture.

Titrations of virus in pulmonary tissues. Animals were sacrificed by carbon dioxide intoxication. After the thoracic wall was removed aseptically, the lungs were dissected from the heart, and homogenized in a TenBroeck tissue grinder in 10 parts (v:w) of Hanks, balanced salt solution, modified for stabilizing virus by the addition of 0.218 M sucrose, 4.4 mM glutamate, 3.8 mM $KH_2PO_4$ and 7.2 mM $K_2HPO_4$. After low-speed centrifugation, serial ten-fold dilutions of homogenate, each in duplicate, were applied to cell monolayers in multi-well culture dishes. HEp-2 cells were used for RSV assay, and MA-104 cells for PIV3 assay. After four days incubation at 37° C. under methylcellulose overlay, the cells were stained with crystal violet in glutaraldehyde solution, and the plaques counted. Viral titers were expressed as a geometric mean, plus or minus the standard error, for all animals (a minimum of four) at a given time point. The Student t-test of summary data was used to compare different treatment groups.

IgG. Purified human IgG (Sandoglobulin, manufactured by Sandoz, Ltd., Basel, Switzerland), with high neutralizing titer against either RSV or PIV3, was used. Several lots of Sandoglobulin were screened, and two lots with high titer against RSV and PIV3, respectively, were set aside in sufficient quantity to perform all of the experiments.

Histopathology studies. After animals were sacrificed by carbon dioxide intoxication, the chest cavity was opened, and the heart and lungs removed intact. The trachea was cannulated with a blunt needle, the lungs inflated with 10% neutral buffered formalin to their normal volume, and the trachea tied with a suture. Coronal sections of the lungs were cut at a thickness of 4 microns, and stained with hematoxylin and eosin.

Standard published pathologic criteria for the identification and scoring of bronchiolitis and interstitial pneumonia were used (Porter, 1991 J. Virol. 65:103–111). Briefly, bronchiolitis is the accumulation of inflammatory cells, mostly or exclusively lymphocytes, in and around bronchioles. There may be accompanying damage to the epithelial cells, including loss of cilia or cell death. Interstitial pneumonia is thickening of the alveolar walls, usually accompanied by infiltration of inflammatory cells into the alveolar septae. Bronchiolitis was quantitated by examining each bronchiole within the lung section (generally 40–70 bronchioles) and scoring for the presence or absence of lymphocytic infiltration. The percentage of affected bronchioles was then calculated. Interstitial pneumonia was quantitated by estimating the percentage of affected alveolar tissue in the lung section. A minimum of four animals were examined for each time point. Arithmetic means of pathology scores were calculated, and differences between treatment groups evaluated by the Student t-test of summary data. In each experiment, uninfected animals served as sentinels to rule out the presence of adventitious agents.

TABLE 1

APPENDIX A: INDIVIDUAL ANIMALS CONSTITUTING THE SUMMARY DATA PRESENTED IN TABLE 1-8

| | Treatment | Animal # | % Alveoli | % Bronchioles |
|---|---|---|---|---|
| 1 | Control | 1 | 35 | 60 |
| | (untreated) | 2 | 30 | 56 |
| | | 3 | 10 | 63 |
| | | 4 | 25 | 63 |
| | Mean: | | 25 | 61 |
| | Standard Error: | | 5.40 | 4.31 |
| | Treated | 5 | 5 | 8 |
| | (Hydrocortisone) | 6 | 15 | 10 |
| | | 7 | 15 | 14 |
| | | 8 | 10 | 4 |
| | Mean: | | 11 | 9 |
| | Standard Error: | | 2.39 | 2.08 |
| | Significance vs. Untreated: | | N.S. | p < 0.001 |
| 2 | Control | 9 | 40 | 75 |
| | (untreated) | 10 | 50 | 65 |
| | | 11 | 50 | 62 |
| | | 12 | 25 | 56 |
| | Mean: | | 41 | 65 |
| | Standard Error: | | 5.91 | 9.81 |
| | Treated | 13 | 50 | 16 |
| | (Hydrocortisone) | 14 | 20 | 20 |
| | | 15 | 25 | 6 |
| | | 16 | 25 | 18 |
| | Mean: | | 30 | 15 |

TABLE 1-continued

APPENDIX A: INDIVIDUAL ANIMALS CONSTITUTING THE SUMMARY DATA PRESENTED IN TABLE 1-8

| Treatment | Animal # | % Alveoli | % Bronchioles |
|---|---|---|---|
| Standard Error: | | 6.77 | 3.11 |
| Significance vs. Untreated: | | N.S. | $p < 0.001$ |
| Significance when Exps. 1 and 2 are combined: | | | |
| 6 Control (untreated) | 44 | 55 | 54 |
| | 45 | 80 | 72 |
| | 46 | 90 | 58 |
| Treated (Hydrocortisone) | 53 | 15 | 21 |
| | 54 | 25 | 23 |
| | 55 | 20 | 27 |
| 7 Control (untreated) | 47 | 95 | 96 |
| | 48 | 70 | 86 |
| | 49 | 80 | 93 |
| | 50 | 75 | 98 |
| | 51 | 80 | 98 |
| | 52 | 95 | 100 |
| Treated (Hydrocortisone) | 56 | 10 | 5 |
| | 57 | 60 | 29 |
| | 58 | 40 | 8 |
| Significance when Exps. 1, 2, 6 and 7 are combined: | | | |
| Control (untreated) | | | |
| Mean: | | 58 | 74 |
| Standard Error: | | 6.62 | 4.20 |
| Treated (Hydrocortisone) | | | |
| Mean: | | 24 | 15 |
| Standard Error: | | 4.23 | 2.22 |
| Significance vs. Untreated: | | $p < 0.001$ | $p < 0.001$ |

TABLE 2

| Experiment # | Treatment | Animal # | % Alveoli | % Bronchioles |
|---|---|---|---|---|
| 3 | Control (untreated) | 17 | 10 | 80 |
| | | 18 | 50 | 56 |
| | | 19 | 20 | 88 |
| | | 20 | 90 | 59 |
| | Mean: | | 43 | 71 |
| | Standard Error | | 17.97 | 7.85 |
| | Treated (Hydrocortisone) | 21 | 10 | 18 |
| | | 22 | 10 | 16 |
| | | 23 | 5 | 21 |
| | | 24 | 9 | 8 |
| | Mean: | | 9 | 16 |
| | Standard Error: | | 1.25 | 2.78 |
| | Significance vs. Untreated: | | N.S. | $p < 0.001$ |
| 4 | Control (untreated) | 25 | 50 | 94 |
| | | 26 | 90 | 83 |
| | | 27 | 80 | 89 |
| | | 28 | 60 | 97 |
| | Mean: | | 70 | 91 |
| | Standard Error: | | 9.13 | 3.07 |

TABLE 2-continued

| Experiment # | Treatment | Animal # | % Alveoli | % Bronchioles |
|---|---|---|---|---|
| | Treated (Hydrocortisone) | 29 | 50 | 26 |
| | | 30 | 40 | 37 |
| | | 31 | 40 | 42 |
| | | 32 | 20 | 50 |
| | Mean | | 38 | 39 |
| | Standard Error: | | 6.29 | 5.02 |
| | Significance vs. Untreated: | | $p < 0.05$ | $p < 0.001$ |
| Significance when Exps. 3 and 4 are combined: | | | $p < 0.02$ | $p < 0.001$ |

TABLE 3

| Experiment # | Treatment | Animal # | % Alveoli | % Bronchioles |
|---|---|---|---|---|
| 5 | Control (untreated) | 33 | 70 | 91 |
| | | 34 | 80 | 82 |
| | | 35 | 50 | 75 |
| | | 36 | 80 | 84 |
| | Mean: | | 70 | 83 |
| | Standard Error: | | 7.07 | 3.29 |
| | Dexamethasone | 37 | 80 | 29 |
| | | 38 | 20 | 21 |
| | | 39 | 50 | 14 |
| | Mean: | | 50 | 21 |
| | Standard Error: | | 17.32 | 4.33 |
| | Significance vs. Untreated: | | N.S. | $p < 0.001$ |
| | Triamcinolone | 40 | 50 | 12 |
| | | 41 | 10 | 4 |
| | | 42 | 30 | 17 |
| | | 43 | 5 | 2 |
| | Mean: | | 24 | 9 |
| | Standard Error: | | 10.28 | 3.50 |
| | Significance vs. Untreated: | | $p < 0.01$ | $p < 0.001$ |

TABLE 4

PULMONARY PATHOLOGY, PIV3

| Treatment | Animal # | % Alveoli | % Bronchioles |
|---|---|---|---|
| Untreated | 33 | 70 | 91 |
| | 34 | 80 | 82 |
| | 35 | 50 | 75 |
| | 36 | 80 | 84 |
| Mean: | | 70 | 83 |
| Standard Error: | | 7.07 | 3.29 |
| Triamcinolone | 40 | 50 | 12 |
| | 41 | 10 | 4 |
| | 42 | 30 | 17 |
| | 43 | 5 | 2 |
| Mean: | | 24 | 9 |
| Standard Error: | | 10.28 | 3.5 |
| Significance vs. Untreated | | $p < 0.01$ | $p < 0.001$ |

TABLE 5

PULMONARY VIRAL TITERS (pfu/gram), PIV3

| | Day 6 | | Day 8 | | Day 10 | |
|---|---|---|---|---|---|---|
| Treatment | Animal # | Viral Titer | Animal # | Viral Titer | Animal # | Viral Titer |
| Untreated | 59 | $10^{3.2}$ | 64 | $<10^{2.0}$ | 69 | $<10^{2.0}$ |
| | 60 | $10^{2.6}$ | 65 | $<10^{2.0}$ | 70 | $<10^{2.0}$ |
| | 61 | $<10^{2.0}$ | 66 | $<10^{2.0}$ | 71 | $<10^{2.0}$ |
| | 62 | $10^{2.0}$ | 67 | $<10^{2.0}$ | 72 | $<10^{2.0}$ |
| | 63 | $10^{2.8}$ | 68 | $<10^{2.0}$ | 73 | $<10^{2.0}$ |
| Geometric mean: | | $10^{2.54}$ | | $<10^{2.0}$ | | $<10^{2.0}$ |
| Standard Error: | | $10^{0.24}$ | | 0 | | 0 |
| Triamcinolone | 74 | $10^{5.0}$ | 79 | $10^{4.8}$ | 83 | $10^{5.1}$ |
| | 75 | $10^{5.3}$ | 80 | $10^{5.0}$ | 84 | $10^{3.3}$ |
| | 76 | $10^{5.6}$ | 81 | $10^{5.1}$ | 85 | $10^{4.4}$ |
| | 77 | $10^{5.4}$ | 82 | $10^{5.0}$ | 86 | $10^{4.4}$ |
| | 78 | $10^{4.9}$ | | | | |
| Geometric Mean: | | $10^{5.23}$ | | $10^{4.96}$ | | $10^{4.32}$ |
| Standard Error: | | $10^{0.13}$ | | $10^{0.08}$ | | $10^{0.38}$ |

TABLE 5-continued

| | PULMONARY VIRAL TITERS (pfu/gram), PIV3 | | | | | |
|---|---|---|---|---|---|---|
| | Day 6 | | Day 8 | | Day 10 | |
| Treatment | Animal # | Viral Titer | Animal # | Viral Titer | Animal # | Viral Titer |
| Signif. vs. Untreated | | $p < 0.001$ | | $p < 0.001$ | | $p < 0.001$ |

TABLE 6

| | PULMONARY PATHOLOGY AND VIRAL TITERS, PIV3 | | | | |
|---|---|---|---|---|---|
| Treatment | Animal # | % Alveoli | % Bronchioles | Animal # | Day 6 Titer |
| Untreated | 87 | 15 | 19 | 91 | $10^{3.4}$ |
| | 88 | 35 | 95 | 92 | $10^{2.7}$ |
| | 89 | 20 | 84 | 93 | $10^{3.1}$ |
| | 90 | 50 | 92 | 94 | $10^{3.1}$ |
| Mean: | | 31 | 74 | Geometric Mean: | $10^{3.1}$ |
| Standard Error: | | 7.47 | 17.98 | Standard Error: | $10^{0.14}$ |
| Triamcinolone | 95 | 5 | 7 | 99 | $10^{4.6}$ |
| | 96 | 10 | 8 | 100 | $10^{4.6}$ |
| | 97 | 0 | 4 | 101 | $10^{4.4}$ |
| | 98 | 25 | 5 | 102 | $10^{4.7}$ |
| Mean: | | 10 | 6 | Geometric Mean: | $10^{4.58}$ |
| Standard Error: | | 5.4 | 0.91 | Standard Error: | $10^{0.06}$ |
| Signif. vs. Untreated: | | $p < 0.05$ | $< 0.001$ | | $p < 0.001$ |
| IgG | 103 | 60 | 93 | 107 | $< 10^{2.0}$ |
| | 104 | 70 | 81 | 108 | $< 10^{2.0}$ |
| | 105 | 90 | 99 | 109 | $< 10^{2.0}$ |
| | 106 | 80 | 93 | 110 | $< 10^{2.0}$ |
| Mean: | | 75 | 92 | Geometric Mean: | $< 10^{2.0}$ |
| Standard Error: | | 6.45 | 3.77 | Standard Error: | 0 |
| Signif. vs. Untreated: | | N.S. | N.S. | | $p < 0.001$ |
| Triamcinolone + IgG | 111 | 5 | 2 | 114 | $10^{3.0}$ |
| | 112 | 5 | 2 | 115 | $10^{2.0}$ |
| | 113 | 10 | 2 | 116 | $10^{2.6}$ |
| | | | | 117 | $10^{2.6}$ |
| Mean: | | 7 | 2 | | $10^{2.4}$ |
| Standard Error: | | 1.67 | 0 | | $10^{0.25}$ |
| Signif. vs. Untreated: | | $p < 0.05$ | $p < 0.025$ | | N.S. |

TABLE 7

| | PULMONARY PATHOLOGY AND VIRAL TITERS, RSV | | | |
|---|---|---|---|---|
| Treatment | Animal # | % Bronchioles | Animal # | Day 6 Titer |
| Untreated | 118 | 17 | 122 | $10^{3.5}$ |
| | 119 | 24 | 123 | $10^{3.4}$ |
| | 120 | 6 | 124 | $10^{3.4}$ |
| | 121 | 39 | 125 | $10^{3.3}$ |
| Mean: | | 21.5 | Geometric mean: | $10^{3.4}$ |
| Standard Error: | | 6.91 | Standard Error: | $10^{0.04}$ |
| Triamcinolone | 126 | 0 | 130 | $10^{4.7}$ |
| | 127 | 2 | 131 | $10^{4.6}$ |
| | 128 | 0 | 132 | $10^{4.7}$ |
| | 129 | 0 | 133 | $10^{5.0}$ |
| Mean: | | 0.5 | Geometric mean: | $10^{4.8}$ |
| Standard Error: | | 0.5 | Standard Error: | $10^{0.08}$ |
| Significance vs. Untreated | | $p < 0.025$ | | $p < 0.001$ |
| IgG | 134 | 32 | 138 | $< 10^{2.0}$ |
| | 135 | 3 | 139 | $< 10^{2.0}$ |
| | 136 | 25 | 140 | $< 10^{2.0}$ |
| | 137 | 48 | 141 | $< 10^{2.0}$ |
| Mean: | | 27 | Geometric mean: | $< 10^{2.0}$ |
| Standard Error: | | 9.34 | Standard Error: | 0 |
| Significance v. Untreated | | N.S. | | $p < 0.001$ |
| Triamcinolone + IgG | 142 | 0 | 146 | $< 10^{2.0}$ |
| | 143 | 0 | 147 | $< 10^{2.0}$ |
| | 144 | 2 | 148 | $10^{2.0}$ |
| | 145 | 0 | 149 | $< 10^{2.0}$ |
| Mean: | | 0.5 | Geometric mean: | $10^{2.0}$ |
| Standard Error: | | 0.5 | Standard Error: | 0 |
| Significance vs. Untreated | | $p < 0.025$ | | $p < 0.001$ |

TABLE 8

| | PULMONARY PATHOLOGY AND VIRAL TITERS, RSV | | | |
|---|---|---|---|---|
| Treatment | Animal # | % Bronchioles | Animal # | Day 6 Titer |
| Untreated | 150 | 51 | 154 | $10^{3.8}$ |
| | 151 | 10 | 155 | $10^{3.6}$ |
| | 152 | 52 | 156 | $10^{4.6}$ |

TABLE 8-continued

PULMONARY PATHOLOGY AND VIRAL TITERS, RSV

| Treatment | Animal # | % Bronchioles | Animal # | Day 6 Titer |
|---|---|---|---|---|
| | 153 | 42 | 157 | $10^{3.9}$ |
| Mean: | | 38 | Geometric mean: | $10^{3.8}$ |
| Standard Error: | | 9.84 | Standard Error: | $10^{0.14}$ |
| Triamcinolone | 158 | 0 | 162 | $10^{5.0}$ |
| | 159 | 0 | 163 | $10^{4.9}$ |
| | 160 | 0 | 164 | $10^{5.1}$ |
| | 161 | 0 | 165 | $10^{5.4}$ |
| Mean: | | 0 | Geometric mean: | $10^{5.2}$ |
| Standard Error: | | 0 | Standard Error: | $10^{0.11}$ |
| Significance vs. Untreated | | $p < 0.001$ | | $p < 0.001$ |
| Ribavirin | 166 | 61 | 170 | $10^{4.1}$ |
| | 167 | 31 | 171 | $10^{4.7}$ |
| | 168 | 49 | 172 | $10^{4.1}$ |
| | 169 | 52 | 173 | $10^{4.3}$ |
| Mean: | | 48 | Geometric mean: | $10^{4.2}$ |
| Standard Error: | | 6.29 | Standard Error: | $10^{0.14}$ |
| Significance vs. Untreated: | | N.S. | | N.S. |
| Triamcinolone + Ribavirin | 174 | 0 | 178 | $10^{5.0}$ |
| | 175 | 0 | 179 | $10^{5.0}$ |
| | 176 | 2 | 180 | $10^{5.1}$ |
| | 177 | 0 | 181 | $10^{5.1}$ |
| Mean: | | 0.5 | Geometric mean: | $10^{5.1}$ |
| Standard Error: | | 0.5 | Standard Error: | $10^{0.02}$ |
| Significance vs. Untreated: | | $p < 0.01$ | | $p < 0.001$ |

What is claimed is:

1. A method of treating pneumonia in a host, susceptible to or suffering from pneumonia caused by a microorganism selected from a virus, a bacterium, a fungus, and Pneumocystis carinii, comprising administering directly into the lower respiratory tract of the host an anti-inflammatory agent selected from a corticosteroid, indomethacin, ibuprofen, and acetylsalicylic acid at a dosage of from 0.1 μg to 1000 mg/kg body weight of the host to reduce inflammation and an anti-infectious agent with activity against said microorganism at a dosage of from 0.1 μg to 1000 mg/kg body weight of the host to reduce the concentration of said microorganism; the anti-inflammatory agent and the anti-infectious agent being administered in the form of a small particle aerosol having a size less than 10 microns.

2. The method of claim 1, wherein the anti-infectious agent is administered topically, orally, intravenously, or intraperitoneally.

3. The method of claim 1, wherein the anti-inflammatory agent is a corticosteroid.

4. The method of claim 3, wherein the corticosteroid is selected from the group consisting of cortisone, hydrocortisone, triamcinolone, dexamethasone, and beclamethasone.

5. The method of claim 1, wherein the anti-inflammatory agent is administered intranasally.

6. The method of claim 1, wherein the microorganism is influenza virus type A, influenza virus type B, influenza virus type C, parainfluenza virus type 1, parainfluenza virus type 2, parainfluenza virus type 3, respiratory syncytial virus, a respiratory coronavirus, or a respiratory adenovirus.

7. The method of claim 1, wherein the microorganism is parainfluenza virus type 3, respiratory syncytial virus, or adenovirus type 5.

8. The method of claim 1, wherein the anti-infectious agent is an antibody to said microorganism.

9. The method of claim 8, wherein the antibody is a polyclonal or monoclonal antibody.

10. The method of claim 1, wherein the anti-infectious agent is human immunoglobulin which comprises antibodies to said microorganism.

11. The method of claim 10, wherein said human immunoglobulin is human immunoglobulin G in a dosage of from 0.1 μg to 100 mg/kg body weight of the host.

12. The method of claim 10, wherein said microorganism is respiratory syncytial virus or parainfluenza virus type 3.

13. The method of claim 1, wherein the anti-infectious agent is an anti-bacterial agent, antifungal agent, anti-parasitic agent, or anti-viral agent.

14. The method of claim 1, wherein the anti-infectious agent is an anti-viral agent selected from the group consisting of ribavirin and amantidine.

15. The method of claim 1, wherein the host is a mammal.

16. The method of claim 1, wherein the host is a human.

17. A method of treating pneumonia in a human, susceptible to or suffering from pneumonia caused by respiratory syncytial virus or parainfluenza virus type 3, comprising administering directly into the lower respiratory tract of the human an anti-inflammatory agent selected from a corticosteroid, indomethacin, ibuprofen, and acetylsalicylic acid at a dosage of from 0.1 μg to 1000 mg/kg body weight of the host to reduce inflammation and an human immunoglobulin G at a dosage of from 0.1 μg to 100 mg/kg body weight of the host to reduce the concentration of the respiratory syncytial virus or parainfluenza virus type 3, the anti-inflammatory agent and the anti-infectious agent being administered in the form of a small particle aerosol having a size less than 10 microns.

18. The method of claim 17, wherein the anti-inflammatory agent is a corticosteroid.

19. A method of treating pneumonia in a host, susceptible to or suffering from pneumonia caused by parainfluenza virus type 3, adenovirus type 5, or respiratory syncytial virus, comprising administering directly into the lower respiratory tract of the host an anti-inflammatory agent selected from a corticosteroid, indomethacin, ibuprofen, and acetylsalicylic acid at a dosage of from 0.1 μg to 1000 mg/kg body weight of the host to reduce inflammation and an anti-infectious agent with activity against said virus at a dosage of from 0.1 μg to 1000 mg/kg body weight of the host to reduce the concentration of said virus, the anti-inflammatory agent and the anti-infectious agent being administered in the form of a small particle aerosol having a size less than 10 microns.

20. A medication that comprises aerosol particles having a size of less than 10 microns comprising an anti-infectious agent with activity against an infectious agent at a dosage of from 0.1 μg to 1000 mg/kg body weight of a host to reduce the concentration of said infectious agent and an anti-inflammatory agent selected from a corticosteroid, indomethacin, ibuprofen, and acetylsalicylic acid at a dosage of from 0.1 μg to 1000 mg/kg body weight of the host to reduce inflammation.

21. The method of claim 1 wherein the anti-inflammatory agent is administered at a dosage of 2 μg to 0.2 mg/kg and the anti-infectious agent is administered at a dosage of 2 μg to 20 mg/kg.

22. A method of treating pneumonia in a host, susceptible to or suffering from pneumonia caused by a microorganism selected from a virus, a bacterium, a fungus, and *Pneumocystis carinii*, comprising topically administering directly into the lower respiratory tract of the host an anti-inflammatory agent selected from a corticosteroid, indomethacin, ibuprofen, and acetylsalicylic acid at a dosage of from 0.1 82 g to 1000 mg/kg body weight of the host to reduce inflammation and an human immunoglobulin G at a dosage of from 0.1 μg to 100 mg/kg body weight of the host to reduce the concentration of said microorganism, the anti-inflammatory agent and the human immunoglobulin G being administered in the form of a small particle aerosol having a size less than 10 microns.

* * * * *